(12) United States Patent
Lin

(10) Patent No.: US 8,143,214 B2
(45) Date of Patent: *Mar. 27, 2012

(54) PROTEIN-POLYMER CONJUGATES

(75) Inventor: Ko-Chung Lin, Lexington, MA (US)

(73) Assignee: PharmaEssentia Corp., Taipei (TW)

(*) Notice: Subject to any disclaimer, the term of this patent is extended or adjusted under 35 U.S.C. 154(b) by 465 days.

This patent is subject to a terminal disclaimer.

(21) Appl. No.: 12/192,485

(22) Filed: Aug. 15, 2008

(65) Prior Publication Data

US 2009/0053177 A1 Feb. 26, 2009

Related U.S. Application Data

(60) Provisional application No. 60/956,273, filed on Aug. 16, 2007.

(51) Int. Cl.
- *A61K 38/21* (2006.01)
- *A61K 38/00* (2006.01)
- *C07K 14/00* (2006.01)
- *C07K 14/52* (2006.01)
- *A61P 31/00* (2006.01)

(52) U.S. Cl. .......... 514/4.3; 514/1.1; 514/7.4; 514/11.4; 530/350; 530/351; 424/85.7

(58) Field of Classification Search .................. None
See application file for complete search history.

(56) References Cited

U.S. PATENT DOCUMENTS

| | | | |
|---|---|---|---|
| 5,643,575 A | 7/1997 | Martinez | |
| 5,824,784 A | 10/1998 | Kinstler | |
| 5,919,455 A | 7/1999 | Greenwald | |
| 5,932,462 A | 8/1999 | Harris | |
| 5,951,974 A | 9/1999 | Gilbert | |
| 5,985,265 A | 11/1999 | Kinstler | |
| 7,090,835 B2 | 8/2006 | Gabriel | |
| 7,125,843 B2* | 10/2006 | DeFrees et al. | 514/13.5 |
| 7,157,546 B2 | 1/2007 | Kozlowski | |
| 2005/0009988 A1 | 1/2005 | Harris | |
| 2005/0107277 A1 | 5/2005 | Lin et al. | |
| 2005/0143292 A1* | 6/2005 | DeFrees et al. | 514/8 |

FOREIGN PATENT DOCUMENTS

| | | |
|---|---|---|
| CN | 1966547 | 5/2007 |
| CN | 1970572 | 5/2007 |
| CN | 101002944 | 7/2007 |
| CN | 101104078 | 1/2008 |
| CN | 101108895 | 1/2008 |
| CN | 101491682 | 7/2009 |
| CN | 101514229 | 8/2009 |
| CN | 101671390 | 3/2010 |
| WO | 2004/022630 | 3/2004 |
| WO | 2006/024953 | 3/2006 |
| WO | WO 2006/095029 * | 9/2006 |
| WO | 2009030066 | 12/2006 |
| WO | 2009030065 | 12/2009 |

OTHER PUBLICATIONS

Definition of moiety from http://dictionary.reference.com/browse/moiety, pp. 1-3. Accessed Aug. 26, 2010.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Webster, et al, "Pegylation of Somatropin (Recombinant Human Growth Hormone): Impact on Its Clearance in Humans", Xenobiotica, Oct. 2008; 38(10): 1340-1351.
Pascal Bailon et al., Rational Design of a Potent, Long-Lasting Form of Interferon: A 40KDa Branched Polyethylene Glycol-Conjugated Interferon alpha-2a for the Treatment of Hepatitis C,Bioconjugate Chemistry, Feb. 16, 2001, vol. 12, pp. 195-202.
Jing Li and W.John Kao, Synthesis of Polyethylene Glycol(PEG) Derivatives and PEGylated-Peptide Biopolymer Conjugate, Biomacromolecules, May 17, 2003. vol. 4, pp. 1055-1067.
Samuel Zalipsky, Chemistry of Polyethylene Glycol Conjugates with Biologically Active Molecules, Advanced Drug Delivery Reviews, Sep. 30, 1995, vol. 16, pp. 157-182.

* cited by examiner

Primary Examiner — Julie Ha
(74) Attorney, Agent, or Firm — Occhiuti Rohlicek & Tsao LLP

(57) ABSTRACT

Protein-polymer conjugates are described. Also described are a method for preparing a protein-polymer conjugate and its use in treating hepatitis B virus or hepatitis C virus infection.

12 Claims, No Drawings

SEQUENCE LISTING

<160> NUMBER OF SEQ ID NOS: 9

<210> SEQ ID NO 1
<211> LENGTH: 188
<212> TYPE: PRT
<213> ORGANISM: Homo sapiens

<400> SEQUENCE: 1

```
Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185
```

<210> SEQ ID NO 2
<211> LENGTH: 165
<212> TYPE: PRT
<213> ORGANISM: Homo sapiens

<400> SEQUENCE: 2

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125
```

Tyr Leu Lys Glu Lys Tyr Ser Pro Cys Ala Trp Glu Val Val Arg
            130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 3
<211> LENGTH: 166
<212> TYPE: PRT
<213> ORGANISM: Homo sapiens

<400> SEQUENCE: 3

Met Cys Asp Leu Pro Gln Thr His Ser Leu Gly Ser Arg Arg Thr Leu
1               5                   10                  15

Met Leu Leu Ala Gln Met Arg Arg Ile Ser Leu Phe Ser Cys Leu Lys
            20                  25                  30

Asp Arg His Asp Phe Gly Phe Pro Gln Glu Glu Phe Gly Asn Gln Phe
        35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 4
<211> LENGTH: 195
<212> TYPE: PRT
<213> ORGANISM: Homo sapiens

<400> SEQUENCE: 4

Met Ala Leu Leu Phe Pro Leu Leu Ala Ala Leu Val Met Thr Ser Tyr
1               5                   10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60

Met Val Lys Gly Ser Gln Leu Gln Lys Ala His Val Met Ser Val Leu
65                  70                  75                  80

His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Glu Leu
            100                 105                 110

His Gln Gln Leu Gln His Leu Glu Thr Cys Leu Leu Gln Val Val Gly

```
                    115                 120                 125
Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
            180                 185                 190

Gly Ser Ser
        195

<210> SEQ ID NO 5
<211> LENGTH: 176
<212> TYPE: PRT
<213> ORGANISM: Homo sapiens

<400> SEQUENCE: 5

Leu Ser Tyr Lys Ser Ile Cys Ser Leu Gly Cys Asp Leu Pro Gln Thr
1               5                   10                  15

His Ser Leu Gly Asn Arg Arg Ala Leu Ile Leu Leu Ala Gln Met Gly
                20                  25                  30

Arg Ile Ser Pro Phe Ser Cys Leu Lys Asp Arg His Asp Phe Gly Leu
            35                  40                  45

Pro Gln Glu Glu Phe Asp Gly Asn Gln Phe Gln Lys Thr Gln Ala Ile
        50                  55                  60

Ser Val Leu His Glu Met Ile Gln Gln Thr Phe Asn Leu Phe Ser Thr
65                  70                  75                  80

Glu Asp Ser Ser Ala Ala Trp Glu Gln Ser Leu Leu Glu Lys Phe Ser
                85                  90                  95

Thr Glu Leu Tyr Gln Gln Leu Asn Asn Leu Glu Ala Cys Val Ile Gln
            100                 105                 110

Glu Val Gly Met Glu Glu Thr Pro Leu Met Asn Glu Asp Ser Ile Leu
        115                 120                 125

Ala Val Arg Lys Tyr Phe Gln Arg Ile Thr Leu Tyr Leu Thr Glu Lys
    130                 135                 140

Lys Tyr Ser Pro Cys Ala Trp Glu Val Val Arg Ala Glu Ile Met Arg
145                 150                 155                 160

Ser Leu Ser Phe Ser Thr Asn Leu Gln Lys Arg Leu Arg Arg Lys Asp
                165                 170                 175

<210> SEQ ID NO 6
<211> LENGTH: 217
<212> TYPE: PRT
<213> ORGANISM: Homo sapiens

<400> SEQUENCE: 6

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80
```

-continued

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Ile Gln Ser Trp
            100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
        130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe
            210                 215

<210> SEQ ID NO 7
<211> LENGTH: 191
<212> TYPE: PRT
<213> ORGANISM: Homo sapiens

<400> SEQUENCE: 7

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 8
<211> LENGTH: 193
<212> TYPE: PRT
<213> ORGANISM: Homo sapiens

<400> SEQUENCE: 8

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 9
<211> LENGTH: 166
<212> TYPE: PRT
<213> ORGANISM: Homo sapiens

<400> SEQUENCE: 9

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Lys Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165
```

PROTEIN-POLYMER CONJUGATES

CROSS-REFERENCE TO RELATED APPLICATION PARAGRAPH

This application claims the benefit of U.S. Provisional Application No. 60/956,273 filed on Aug. 16, 2007. The contents of which, is hereby incorporated by reference in its entirety

BACKGROUND

Advance in cell biology and recombinant protein technologies has led to the development of protein therapeutics.

Yet, major hurdles still exist. Most proteins are susceptible to proteolytic degradation and therefore have a short half-life in the circulating system. Other disadvantages include low water solubility and inducement of neutralizing antibodies.

Attachment of a polymer, e.g., polyethylene glycol (PEG), to a protein hinders access of proteolytic enzymes to the protein backbone, resulting in enhanced protein stability. In addition, it may also improve water solubility and minimize immunogenicity. There is a need for effective methods of attaching polymer to proteins.

SUMMARY

An aspect of the present invention relates to a substantially pure (≧80% pure) conjugate containing one or more polymer moieties, a protein moiety, and a linker. In the conjugate, the polymer moiety or moieties are attached to the linker; the nitrogen atom of the N-terminus of the protein moiety is bonded to the linker; the linker is a covalent bond, $C_{1-10}$ alkylene, $C_{2-10}$ alkenylene, or $C_{2-10}$ alkynylene; and the protein moiety is an interferon-α moiety, a human growth hormone moiety, or an erythropoietin moiety. Preferably, the conjugate has a purity of 90% or higher. This conjugate has an unexpected long in vivo half-life.

Another aspect of the present invention relates to protein-polymer conjugates of formula I:

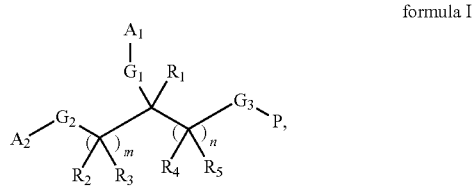

formula I in which each of $R_1$, $R_2$, $R_3$, $R_4$, and $R_5$, independently, is H, $C_{1-5}$ alkyl, $C_{2-5}$ alkenyl, $C_{2-5}$ alkynyl, aryl, heteroaryl, $C_{3-8}$ cycloalkyl, or $C_{3-8}$ heterocycloalkyl; each of $A_1$ and $A_2$, independently, is a polymer moiety; each of $G_1$, $G_2$, and $G_3$, independently, is a bond or a linking functional group; P is a protein moiety; m is 0 or an integer of 1-10; and n is an integer of 1-10.

Referring to the above formula, the protein-polymer conjugate may have one or more of the following features: $G_3$ is a bond and P is a protein moiety in which the amino group at the N-terminus is attached to $G_3$; $A_1$ and $A_2$ are polyalkylene oxide moieties having a molecular weight of 2-100 kD (preferably 10-30 kD), each of $G_1$ and $G_2$ is

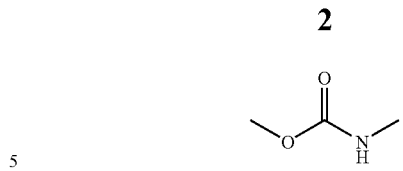

(in which O is attached to $A_1$ or $A_2$, and NH is attached to a carbon atom as shown in formula I), or each of $G_1$ and $G_2$ is urea, sulfonamide, or amide, (in which N is attached to a carbon atom as shown in formula I); m is 4, n is 2, and each of $R_1$, $R_2$, $R_3$, $R_4$, and $R_5$ is H; and P is an interferon moiety or a modified interferon moiety containing 1-4 additional amino acid residues.

The term "alkyl" refers to a mono-valent straight-chained or branched hydrocarbon radical. Examples of alkyl groups include methyl, ethyl, n-propyl, isopropyl, tert-butyl, and n-pentyl. Similarly, the term "alkenyl" or "alkynyl" refers to a mono-valent straight-chained or branched hydrocarbon radical containing one or more C=C double bonds or one or more C≡C triple bonds.

The term "alkylene" refers to a bi-valent straight-chained or branched hydrocarbon radical. Similarly, the term "alkenylene" or "alkynylene" refers to a bi-valent straight-chained or branched hydrocarbon radical containing one or more C=C double bonds or one or more C≡C triple bonds.

The term "aryl" refers to a hydrocarbon ring system (mono-cyclic or bi-cyclic) having at least one aromatic ring. Examples of aryl moieties include, but are not limited to, phenyl, naphthyl, and pyrenyl.

The term "heteroaryl" refers to a hydrocarbon ring system (mono-cyclic or bi-cyclic) having at least one aromatic ring which contains at least one heteroatom such as O, N, or S as part of the ring system and the reminder being carbon. Examples of heteroaryl moieties include, but are not limited to, furyl, pyrrolyl, thienyl, oxazolyl, imidazolyl, thiazolyl, pyridinyl, pyrimidinyl, quinazolinyl, and indolyl.

The term "cycloalkyl" refers to a partially or fully saturated mono-cyclic or bi-cyclic ring system having only carbon ring atoms. Examples include, but are not limited to, cyclopropanyl, cyclopentanyl, and cyclohexanyl.

The term "heterocycloalkyl" refers to a partially or fully saturated mono-cyclic or bi-cyclic ring system having, in addition to carbon, one or more heteroatoms (e.g., O, N, or S), as ring atoms. Examples include, but are not limited to, piperidine, piperazine, morpholine, thiomorpholine, and 1,4-oxazepane.

Alkyl, alkenyl, alkynyl, aryl, heteroaryl, cycloalkyl, and heterocycloalkyl mentioned herein include both substituted and unsubstituted moieties. Examples of substituents include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyamino, alkoxyamino, $C_1$-$C_{10}$ alkylsulfonamide, arylsulfonamide, hydroxy, halogen, thio, $C_1$-$C_{10}$ alkylthio, arylthio, cyano, nitro, acyl, acyloxy, carboxyl, and carboxylic ester.

The term "polyalkylene oxide moiety" refers to a mono-valent radical derived from linear, branched, or star-shaped polyalkylene oxide. The molecular weight of a polyalkylene oxide moiety may be 2-100 kD. The polyalkylene oxide moiety is either saturated or unsaturated. Examples of a polyalkylene oxide moiety include, but are not limited to, polyethylene oxide, polyethylene glycol, polyisopropylene oxide, polybutenylene oxide, and copolymers thereof. Other polymers such as dextran, polyvinyl alcohols, polyacrylamides, or carbohydrate-based polymers can also be used to replace the polyalkylene oxide moiety, as long as they are not antigenic, toxic, or eliciting immune response. The polyalkylene oxide moiety is either substituted or unsubstituted. For example, it can be methoxy-capped polyethylene glycol (mPEG).

The term "protein moiety" refers to a mono-valent radical derived from either a naturally occurring protein or a modified protein. The naturally occurring protein can be interferon-α, interferon-β, human growth hormone, erythropoietin and granulocyte colon-stimulating factor, or antibody. The modified protein can be, e.g., a protein containing interferon-α and 1-4 additional amino acid residues at the N-terminus of the interferon. An example of such a modified interferon is

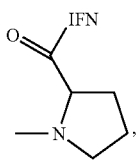

IFN representing an interferon-$\alpha_{2b}$ moiety, the amino group at the N-terminus of which is bonded to the carbonyl group.

The term "interferon-α" refers to a family of highly homologous species-specific proteins that inhibit viral replication and cellular proliferation and modulate immune response. See Bonnem et al., J. Biol. Response Mod., 1984, 3(6):580-598; and Finter, J. Hepatol., 1986, 3 Suppl 2:S157-160.

Many types of interferon-α proteins are commercially available, including Intron-A interferon provided by Schering Corporation, Kenilworth, N.J., Roferon interferon provided by Hoffmann-La Roche, Nutley, N.J., Berofor alpha 2 interferon provided by Boehringer Ingelheim Pharmaceutical, Inc., Ridgefield, Conn., Sumiferon provided by Sumitomo, Japan, and Wellferon interferon alpha-n1 (INS) provided by Glaxo-Wellcome Ltd., London, Great Britain.

Listed below are amino acid sequences of five exemplary human interferon-α proteins, either in precursor form or in mature form:

```
maltfallva llvlscksse svgcdlpqth slgsrrtlml laqmrrislf sclkdrhdfg fpqeefgnqf qkaetipvlh emiqqifnlf stkdssaawd etlldkfyte lyqqlndlea cviqgvgvte tplmkedsil avrkyfqrit lylkekkysp cawevvraei mrsfslstnl qeslrske (SEQ ID NO: 1)
```

(See Krasagakis et al., Cancer Invest. 26 (6), 562-568, 2008)

```
cdlpqthslg srrtlmllaq mrkislfscl kdrhdfgfpq eefgnqfqka etipvlhemi qqifnlfstk dssaawdetl ldkfytelyq qlndleacvi qgvgvtetpl mkedsilavr kyfqritlyl kekkyspcaw evvraeimrs fslstnlqes lrske (SEQ ID NO: 2)
```

(See Klaus, et al., J. Mol. Biol. 274 (4), 661-675, 1997)

```
mcdlpqthsl gsrrtlmlla qmrrislfsc lkdrhdfgfp qeefgnqfqk aetipvlhem iqqifnlfst kdssaawdet lldkfytely qqlndleacv iqgvgvtetp lmkedsilav rkyfqritly lkekkyspca wevvraeimr sfslstnlqe slrske (SEQ ID NO: 3)
```

(See GenBank Accession Number AAP20099, the 30-APR-2003 version.)

```
mallfpllaa lvmtsyspvg slgcdlpqnh gllsrntlvl lhqmrrispf lclkdrrdfr fpqemvkgsq lqkahvmsvl hemlqqifsl fhterssaaw nmtlldqlht elhqqlqhle tcllqvvgeg esagaisspa ltlrryfqgi rvylkekkys dcawevvrme imkslflstn mqerlrskdr dlgss
(SEQ ID NO: 4)
```

(See Capon et al., J. Mol. Cell. Biol. 5 (4):768-779, 1985)

```
lsyksicslg cdlpqthslg nrralillaq mgrispfscl kdrhdfglpq eefdgnqfqk tqaisvlhem iqqtfnlfst edssaaweqs llekfstely qqlnnleacv iqevgmeetp lmnedsilav rkyfqritly ltekkyspca wevvraeimr slsfstnlqk rlrrkd (SEQ ID NO: 5)
```

(See Lund et al., J. Interferon Res. 5 (2), 229-238, 1985)

In one example, the interferon-α protein used for making the conjugate of this invention has an amino acid sequence at least 80% (e.g., 85%, 90%, 95%, or 99%) identical to one of the above listed amino acid sequences, or to the fragment thereof that corresponds to a mature interferon alpha.

The term "human growth hormone" refers to the naturally occurring human growth hormone, either in precursor or mature form, and its functional variants, i.e., having an amino acid sequence at least 80% (e.g., 85%, 90%, 95%, or 99%) identical to the naturally occurring human growth hormone and possessing the same physiological activity of that human growth hormone. The amino acid sequences of the naturally occurring human growth hormone (in precursor and mature form) are shown below:

```
matgsrtsll lafgllclpw lqegsafpti plsrlfdnam lrahrlhqla fdtyqefeea yipkeqkysf lqnpqtslcf sesiptpsnr eetqqksnle llrisllliq swlepvqflr svfanslvyg asdsnvydll kdleegiqtl mgrledgspr tgqifkqtys kfdtnshndd allknyglly cfrkdmdkve tflrivqcrs vegscgf (precursor) (SEQ ID NO: 6)

fptiplsrlf dnamlrahrl hqlafdtyqe feeayipkeq kysflqnpqt slcfsesipt psnreetqqk snlellrisl lliqswlepv qflrsvfans lvygasdsnv ydllkdleeg iqtlmgrled gsprtgqifk qtyskfdtns hnddallkny
```

```
gllycfrkdm dkvetflriv qcrsvegscg f   (mature form)  (SEQ ID NO: 7)
```

Erythropoietin (EPO), produced by either liver or kidney, is a glycoprotein hormone that controls erythropoiesis or red blood cell production. See U.S. Pat. No. 5,621,080. The amino acid sequences of human EPO (in precursor and mature form) are shown below:

```
mgvhecpawl wlllsllslp lglpvlgapp rlicdsrvle rylleakeae nittgcaehc slnenitvpd tkvnfyawkr mevgqqavev wqglallsea vlrgqallvn ssqpweplql hvdkavsglr slttllralg aqkeaisppd aasaaplrti tadtfrklfr vysnflrgkl klytgeacrt gdr (precursor)  (SEQ ID NO: 8)

apprlicdsr vlerylleak eaekittgca ehcslnekit vpdtkvnfya wkrmevgqqa vevwqglall seavlrgqal lvkssqpwep lqlhvdkavs glrslttllr algaqkeais ppdaasaapl rtitadtfrk lfrvysnflr gklklytgea crtgdr   (mature form)  (SEQ ID NO: 9)
```

An erythropoietin protein used to make the conjugate of this invention can be an EPO protein, either in precursor or mature form, produced by a suitable species, e.g., human, murine, swine, and bovine. In one example, the erythropoietin protein has an amino acid sequence at least 80% (e.g., 85%, 90%, 95% or 99%) identical to one of the amino acid sequences shown above.

The "percent identity" of two amino acid sequences is determined using the algorithm of Karlin and Altschul *Proc. Natl. Acad. Sci.* USA 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The term "linking functional group" refers to a bi-valent functional group, one end being connected to the polymer moiety and the other end being connected to the protein moiety. Examples include, but are not limited to, —O—, —S—, carboxylic ester, carbonyl, carbonate, amide, carbamate, urea, sulfonyl, sulfinyl, amino, imino, hydroxyamino, phosphonate, or phosphate group.

The protein-polymer conjugate described above can be in the free form or in the form of salt, if applicable. A salt, for example, can be formed between an anion and a positively charged group (e.g., amino) on a protein-polymer conjugate of this invention. Suitable anions include chloride, bromide, iodide, sulfate, nitrate, phosphate, citrate, methanesulfonate, trifluoroacetate, and acetate. Likewise, a salt can also be formed between a cation and a negatively charged group (e.g., carboxylate) on a protein-polymer conjugate of this invention. Suitable cations include sodium ion, potassium ion, magnesium ion, calcium ion, and an ammonium cation such as tetramethylammonium ion.

In addition, the protein-polymer conjugate may have one or more double bonds, or one or more asymmetric centers. Such a conjugate can occur as racemates, racemic mixtures, single enantiomers, individual diastereomers, diastereomeric mixtures, and cis- or trans- or E- or Z-double bond isomeric forms.

An example the protein-polymer conjugate of this invention is shown below:

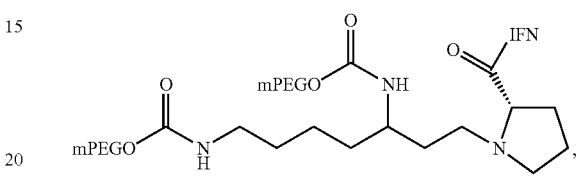

in which mPEG has a molecular weight of 20 kD and IFN is an interferon-$\alpha_{2b}$ moiety.

Still another aspect of this invention relates to compounds which are useful for preparing protein-polymer conjugates. The compounds have formula TI:

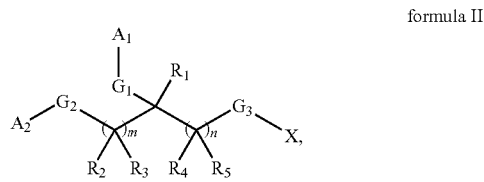

formula II in which X is a reactive group; each of $A_1$ and $A_2$, independently, is a polymer moiety, or one of $A_1$ and $A_2$ is a polymer moiety, and the other is a reactive group; each of $G_1$, $G_2$, and $G_3$, independently, is a bond or a linking functional group; each of $R_1$, $R_2$, $R_3$, $R_4$, and $R_5$, independently, is H, $C_{1-5}$ alkyl, $C_{2-5}$ alkenyl, $C_{2-5}$ alkynyl, aryl, heteroaryl, $C_{3-8}$ cycloalkyl, $C_{3-8}$ heterocycloalkyl, or -$G_4$-X', $G_4$ being a bond or a linking functional group and X' being a reactive group; each m and n, independently, is 0 or an integer of 1-10; provided that if -$G_3$-X is —CO(O)—N-succinimidyl, then n is an integer of 1-10.

In one embodiment, X, X', $A_1$, $A_2$, $G_1$, $G_2$, $G_3$, $G_4$, $R_1$, $R_2$, $R_3$, $R_4$, $R_5$, and m are defined above, and n is an integer of 1-10.

Certain compounds of formula II have one or more of the following features: the polymer moiety may have one or more reactive groups; $G_3$ is a bond and P is a protein moiety in which the amino group at the N-terminus is attached to $G_3$; $A_1$ and $A_2$ are polyalkylene oxide moieties having a molecular weight of 2-100 kD (preferably 12-30 kD), each of $G_1$ and $G_2$ is

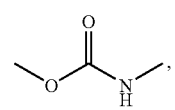

in which O is attached to $A_1$ or $A_2$, and NH is attached to a carbon atom as shown in formula I; m is 4; n is 1; each of $R_1$, $R_2$, $R_3$, $R_4$, and $R_5$ is H; and X is CH(=O) or X is a leaving group (e.g., succinimidyl or p-nitrophenoxy).

The term "reactive group" refers to a functional group that can react with another functional group so that it is either replaced by the other functional group, or is linked to the other function group. A reactive group can be a leaving group, a nucleophilic group, an aldehyde, or a Michael receptor.

The term "leaving group" refers to a functional group that can depart, upon direct displacement or ionization, with the pair of electrons from one of its covalent bonds (see, e.g., F. A. Carey and R. J. Sunberg, Advanced Organic Chemistry, 3rd Ed. Plenum Press, 1990). Examples of a leaving group include, but are not limited to, methanesulfonate, triflate, p-toluenesulfonate, iodine, bromide, chloride, trifluoroacetate, succinimidyl ("Su"), p-nitrophenoxy, and pyridine-2-yl-oxy.

The term "nucleophilic group" refers to an electron-rich functional group, which reacts with an electron-receiving group, such as electrophile, by donating an electron pair.

The term "electrophilic group" refers to an electron-poor functional group, which reacts with an electron-donating group, such as a nucleophile, by accepting an electron pair. Michael receptors are a subset of electrophilic groups. They, upon contacting a nucleophile, undergo Michael reaction. A typical Michael receptor contains an α,β-unsaturated ketone moiety.

Exemplary compounds of formula II are shown below:

PEG Molecules For Coupling With Proteins

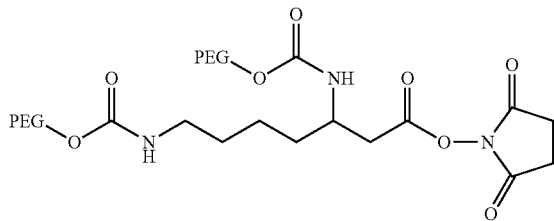
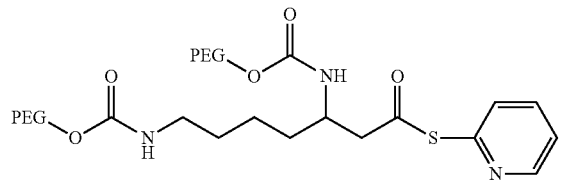
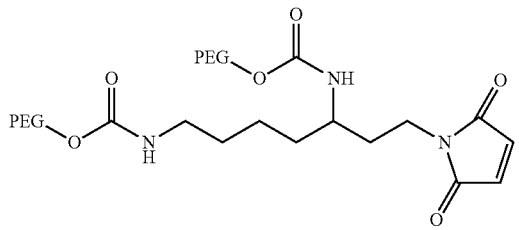
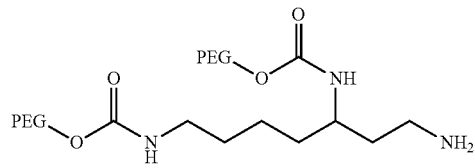
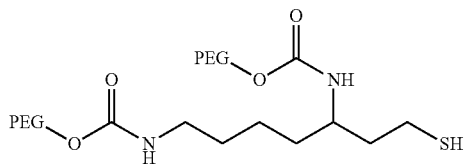
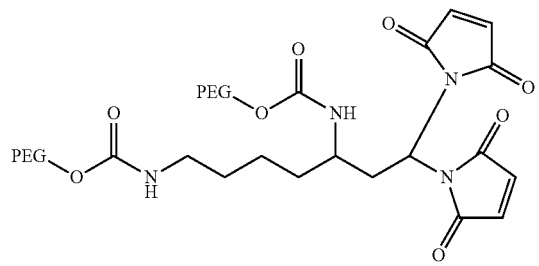
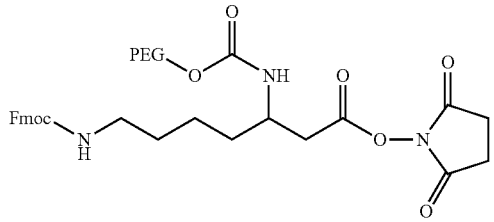
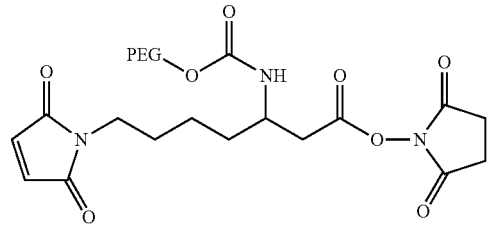
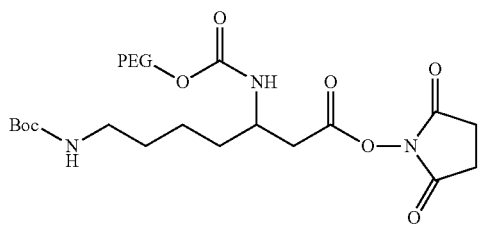
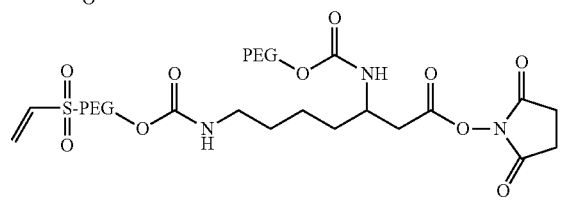

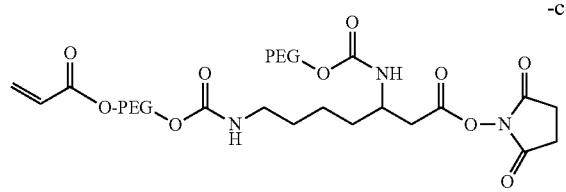
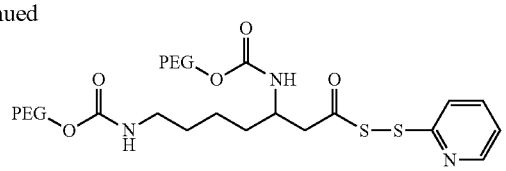

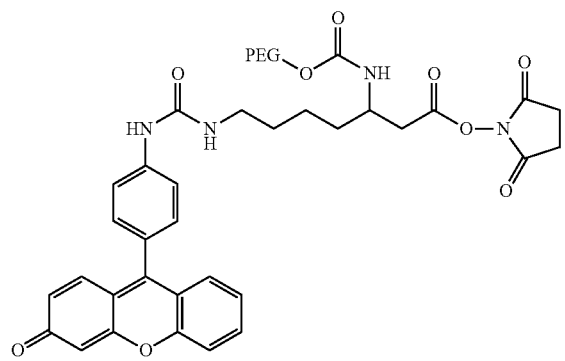

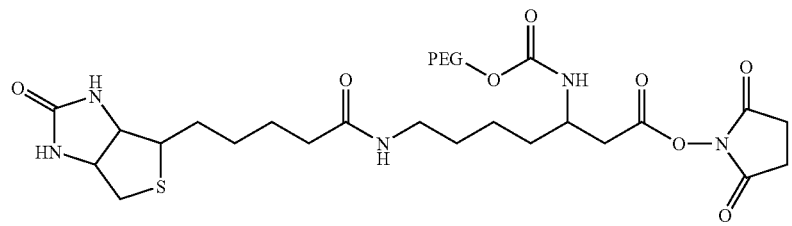

In still another aspect, this invention features a method of preparing protein-polymer conjugates of formula I, in which the amino group at the N-terminus of protein moiety P is attached to linking functional group $G_3$. The method includes coupling an N-terminus free protein H—P with a di-polymer branched molecule of a formula the same as formula II shown above, except that X is a leaving group. The N-terminus free protein H—P refers to a protein in which the nitrogen atom at the terminal amino group of the protein moiety P is bonded to the hydrogen atom H. In other words, H—P has a terminal primary or secondary amino group. Alternatively, the method includes (1) coupling the just-mentioned N-terminus free protein H—P with a di-polymer branched molecule of a formula the same as formula II shown above, except that $G_3$ is a bond, n is 0 or an integer of 1-9, and X is CHO; and (2) reducing the coupling product to form a protein-polymer conjugate.

Interferon is an immunomodulating medication for treating hepatitis B virus (HBV) infection or hepatitis C virus (HCV) infection. In addition, interferon (e.g., interferon-α) can be used to treat non-Hodgkin's lymphoma, Hairy cell leukemia, chronic myelogenous leukemia, AIDS-related Kaposis sarcoma, follicular lymphoma, malignant melanoma, and condyloma accuminata. Thus, another aspect of this invention relates to a method of treating any of the above-mentioned disorders by an interferon-polymer conjugate described herein.

Also within the scope of this invention is a composition containing the an interferon-polymer conjugate for use in any of the above-mentioned disorders, as well as this therapeutic use and use of the conjugate for the manufacture of a medicament for treating one of these disorders.

The details of one or more embodiments of the invention are set forth in the description below. Other features, objects, and advantages of the invention will be apparent from the description and from the claims.

DETAILED DESCRIPTION

Protein-polymer conjugates of the present invention can be prepared by synthetic methods well known in the chemical art. For example, one can bond a linker molecule, concurrently or separately, with two polymer molecules and subsequently bond a protein molecule to the linker molecule to form a protein-polymer conjugate of this invention.

Also within the scope of this invention are the compounds of formula (II). These compounds are useful for making the just-described protein-polymer conjugates. They can be prepared by synthetic methods well known in the chemical art. An illustrative synthetic scheme and an actual example are provided below.

Scheme 1 shows an example of preparing protein-polymer conjugates of this invention. Diamine compound 1, which contains an acetal group, is reacted with N-hydroxysuccinimidyl carbonate mPEG (i.e., compound 2) to form di-PEGylated compound 3, which is subsequently converted to aldehyde 4. This aldehyde compound is reacted with protein having a free amino group via reductive alkylation to afford a protein-polymer conjugate of this invention.

Scheme 1

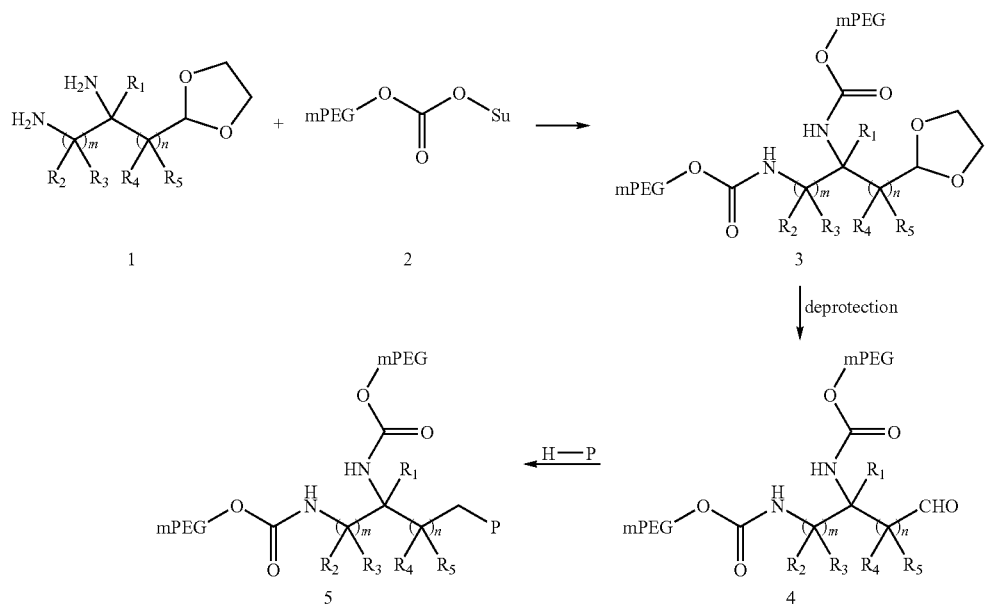

A protein-polymer conjugate thus synthesized can be further purified by a method such as ion exchange chromatography, gel filtration chromatography, electrophoresis, dialysis, ultrafiltration, or ultracentrifugation.

The chemical reactions described above include using solvents, reagents, catalysts, protecting group and deprotecting group reagents, and certain reaction conditions. They may additionally include steps, either before or after the steps described specifically herein, to add or remove suitable protecting groups in order to ultimately allow for synthesis of a protein-polymer conjugate. In addition, various synthetic steps may be performed in an alternate sequence or order to give the desired protein-polymer conjugates. Synthetic chemistry transformations and protecting group methodologies (protection and deprotection) useful in synthesizing applicable protein-polymer conjugates are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The conjugate of the invention has a very high purity. Namely, in 80% or more of the conjugate molecules, the polymer moiety is linked to the same nitrogen atom of the N-terminus of the same protein moiety. In other words, in at least 80% of the conjugate molecules, the protein moiety is identical in all aspects, including its sequence and its bonding position to the polymer moiety.

The conjugate of the invention may be pharmaceutically active in the conjugate form. Alternatively, it can release a pharmaceutically active protein in vivo (e.g., through hydrolysis) by enzymatically cleaving the linkage between the protein moiety and the polymer moiety. Examples of enzymes involved in in vivo cleaving linkages include oxidative enzymes (e.g., peroxidases, amine oxidases, or dehydrogenases), reductive enzymes (e.g., keto reductases), and hydrolytic enzymes (e.g., proteases, esterases, sulfatases, or phosphatases).

Thus, one aspect of this invention relates to a method of administering an effective amount of one or more of the above-described protein-polymer conjugates for treating a disease (e.g., HBV or HCV infection). Specifically, a disease can be treated by administering to a subject one or more of the protein-polymer conjugates in an effective amount. Such a subject can be identified by a health care professional based on results from any suitable diagnostic method.

As used herein, the term "treating" or "treatment" is defined as the application or administration of a composition including a protein-polymer conjugate to a subject (human or animal), who has a disorder, a symptom of the disorder, a disease or disorder secondary to the disorder, or a predisposition toward the disorder, with the purpose to cure, alleviate, relieve, remedy, or ameliorate the disorder, the symptom of the disorder, the disease or disorder secondary to the disorder, or the predisposition toward the disorder. "An effective amount" refers to an amount of a protein-polymer conjugate which confers a therapeutic effect on the treated subject. The therapeutic effect may be objective (i.e., measurably by some tests or markers) or subjective (i.e., a subject gives an indication of or feels an effect).

Also within the scope of this invention is a pharmaceutical composition contains an effective amount of at least one of the protein-polymer conjugates described above and a pharmaceutical acceptable carrier. Further, this invention includes a method of administering an effective amount of one or more of the protein-polymer conjugates to a patient with one or more diseases. Effective doses will vary, as recognized by those skilled in the art, depending on, e.g., the rate of hydrolysis of a protein-polymer conjugate, the types of diseases to be treated, the route of administration, the excipient usage, and the possibility of co-usage with other therapeutic treatment.

To practice the method of the present invention, a composition having one or more of the above-mentioned compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, intraperitoneal, intratracheal or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more of the above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow #10.

Suitable in vitro assays can be used to preliminarily evaluate the efficacy of the above-described conjugates in inhibiting hepatitis B virus or hepatitis C virus. The conjugates can further be examined for its efficacy in treating hepatitis B virus or hepatitis C virus infection by in vivo assays. For example, they can be administered to an animal (e.g., a mouse model) or a human having hepatitis B virus or hepatitis C virus infection and its therapeutic effects are then assessed. Based on the results, dosage ranges and administration routes can also be determined.

The example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Preparation of di-PEG Aldehyde

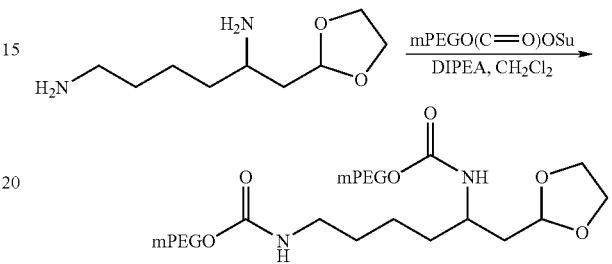

20 kD PEGO(C=O)OSu was prepared from 20 kD mPEGOH purchased from (SunBio Inc., CA, USA) according to the method described in Bioconjugate Chem. 1993, 4, 568-569.

A solution of 6-(1,3-dioxolan-2-yl)hexane-1,5-diamine in dichloromethane (11.97 g of the solution containing 9.03 mg of diamine, 47.8 μmol) was added to a flask containing 20 kD PEGO(C=O)OSu (1.72 g, 86.0 μmol). After PEGO(C=O)OSu was completely dissolved, N,N-diisopropylethylamine (79 μL, 478 μmol) was added. The reaction mixture was stirred at room temperature for 24 h, and then methyl t-butyl ether (200 mL) was added dropwise with stirring. The resulting precipitate was collected and dried under vacuum to give di-PEG acetal (1.69 g, 98%) as a white solid.

$^1$H NMR (400 MHz, d$_6$-DMSO) δ 7.16 (t, J=5.2 Hz, 1H), 7.06 (d, J=8.8 Hz, 1H), 4.76 (t, J=4.8 Hz, 1H), 4.10-3.95 (m, 4H), 1.80-1.65 (m, 1H), 1.65-1.50 (m, 1H), 1.48-1.10 (m, 6H).

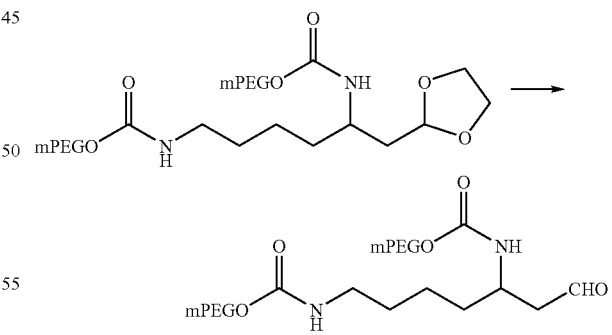

Di-PEG acetal (4.0 g, 0.2 mmol) was suspended in pH 2.0 buffer (critic acid, 40 mL). The reaction mixture was stirred at 35° C. for 24 h and then extracted with dichloromethane (3×50 mL). The combined organic layers were dried over magnesium sulfate, concentrated, and then re-dissolved in dichloromethane (20 mL). The solution was added dropwisely to methyl t-butyl ether (400 mL) with stirring. The resulting precipitate was collected and dried at reduced pressure to give di-PEG aldehyde (3.8 g, 95%) as a white solid.

$^1$H NMR (400 MHz, d$_6$-DMSO) δ 9.60 (s, 1H), 7.24 (d, J=8.4 Hz, 1H), 7.16 (t, J=5.2 Hz, 1H), 4.10-3.95 (m, 4H), 3.95-3.80 (m, 1H), 3.00-2.85 (m, 2H), 2.58-2.36 (m, 2H), 1.46-1.15 (m, 6H).

Preparation of Modified Interferon

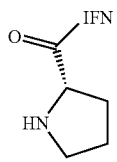

A modified recombinant human interferon-α$_{2b}$ was cloned by a PCR method using human genomic DNA as a template. The oligonucleotides were synthesized based on the flanking sequences of human interferon-α$_{2b}$ (GenBank Accession #J00207, Jan. 8, 2008). The derived PCR products were subcloned into pGEM-T vector (Promega). The IFN variant was PCR amplified again through the pGEM-T clones and subsequently subcloned into protein expression vector pET-24a (Novagen), a T7 RNA polymerase promoter driven vector, using NdeI/BamHI as the cloning sites. Vector pET-24a was then transformed into E. coli BL21-CodonPlus (DE 3)-RIL (Stratagene) strain. The high-expression clones were selected by maintaining the transformed E. coli BL21-CodonPlus (DE 3)-RIL in the presence of karamycin (50 μg/mL) and chloramphenical (50 μg/mL).

Terrific broth medium (BD, 200 mL) was employed for the propagation of BL21-CodonPlus (DE 3)-RIL with Pro-IFN gene in a 1000 mL flask. The flask was shaken at 37° C. at 230 rpm for 16 hr. Batch and fed-batch fermentations were performed in a 5-liter jar fermentor (Bioflo 3000; New Brunswick Scientific Co., Edison, N.J.). The batch fermentation used 150 mL of an overnight preculture inoculum and 3 L of the Terrific broth medium with karamycin (50 μg/mL), chloramphenical (50 ug/mL), 0.4% glycerol, and 0.5% (v/v) trace elements (10 g/L of FeSO$_4$.7H$_2$O, 2.25 g/L of ZnSO$_4$.7H$_2$O, 1 g/L of CuSO$_4$.5H$_2$O, 0.5 g/L of MnSO$_4$H$_2$O, 0.3 g/L of H$_3$BO$_3$, 2 g/L of CaCl$_2$.2H$_2$O, 0.1 g/L of (NH$_4$)$_6$Mo$_7$O$_{24}$, 0.84 g L EDTA, 50 ml/L HCl). The dissolved oxygen concentration was controlled at 35% and the pH was kept at 7.2 by adding a 5 N NaOH aqueous solution. A feeding solution containing 600 g/L of glucose and 20 g/L of MgSO$_4$.7H$_2$O was prepared. When the pH rose to a value greater than the set point, an appropriate volume of the feeding solution was added to increase the glucose concentration in the culture broth. Expression of the Pro-IFN gene was induced by adding IPTG to a final concentration of 1 mM and the culture broth was harvested after incubating for 3 hr.

The collected cell pellet was resuspended with TEN buffer (50 mM Tris-HCl (pH 8.0), 1 mM EDTA, 100 mM NaCl) in an approximate ratio of 1:10 (wet weight g/mL) and disrupted by a microfluidizer, and then centrifuged at 10,000 rpm for 20 min. The pellet containing inclusion body (IB) was washed twice with TEN buffer and centrifuged as described above. The pellet containing IB was then suspended in 150 mL of a 4 M guanidium HCl (GuHCl) aqueous solution and centrifuged at 20,000 rpm for 15 min. The IB was then solubilized in 50 mL of 6 M GuHCl solution. The GuHCl solubilized material was centrifuged at 20,000 rpm for 20 min. Refolding was initiated by dilution of denatured IB in 1.5 L of a freshly prepared refolding buffer (100 mM Tris-HCl (pH 8.0), 0.5 M L-Arginine, 2 mM EDTA) that was stirred only during the addition. The refolding reaction mixture was allowed to incubate for 48 hr without stirring. The refolded recombinant human interferon-α$_{2b}$ (i.e., Pro-IFN) was dialyzed against 20 mM Tris buffer (with 2 mM EDTA and 0.1M urea, pH 7.0) for further purification by Q-Sepharose column chromatography.

The refolded recombinant human protein Pro-IFN was loaded onto a Q-Sepharose column (GE Amersham Pharmacia, Pittsburgh, Pa.). The column was pre-equilibrated and washed with a 20 mM Tris-HCl buffer (pH 7.0). The product was eluted with a mixture of 20 mM Tris-HCl buffer (pH 7.0) and 200 mM NaCl. Fractions containing Pro-IFN was collected based on its absorbance at 280 nm. The concentration of Pro-IFN was determined by a protein assay kit using the Bradford method (Pierce, Rockford, Ill.).

Prepare Protein-Polymer Conjugate

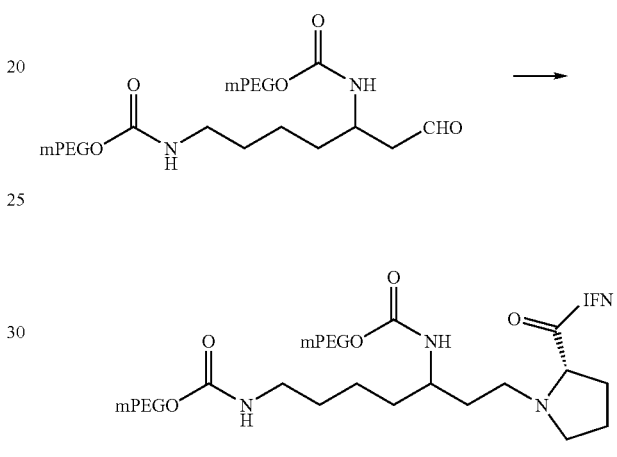

To a solution of di-PEG aldehyde prepared above (1.2 g, 0.03 mmol) in water (72 mL) was added 2 M sodium phosphate buffer (pH 4.0, 5 mL) and Pro-IFN (200 mg in 22.2 mL of pH 7.0 buffer containing 20 mM Tris-HCl and 0.2M NaCl, 0.01 mmol). The reaction mixture was stirred at room temperature for 10 min; then sodium cyanoborohydride aqueous solution (400 mM, 1.25 mL, 0.5 mmol) was added. The reaction mixture was stirred in the dark for 16 h and purified by SP XL Sepharose chromatography. Fractions containing the desired polymer-protein conjugate were collected based on their retention time and absorbance at 280 nm. The concentration of the conjugate was determined by a protein assay kit using the Bradford method (Pierce, Rockford, Ill.). The isolated yield of the conjugate was roughly 40% or higher.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A protein-polymer conjugate of formula I:

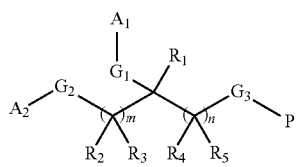

formula I wherein
each of $R_1$, $R_2$, $R_3$, $R_4$, and $R_5$ independently, is H, $C_{1-5}$ alkyl, $C_{2-5}$ alkenyl, $C_{2-5}$ alkynyl, aryl, heteroaryl, $C_{3-8}$ cycloalkyl, or $C_{3-8}$ heterocycloalkyl;
each of $A_1$ and $A_2$, independently, is a polymer;
each of $G_1$, $G_2$, and $G_3$, independently, is a bond or a linking functional group;
P is interferon-$\alpha$, human growth hormone, or erythropoietin;
m is 0 or an integer of 1-10; and
n is an integer of 1-10.

2. The conjugate of claim 1, wherein $G_3$ is a bond and P is a protein in which the amino group at the N-terminus is bonded to $G_3$.

3. The conjugate of claim 2, wherein each of $A_1$ and $A_2$ is mPEG having a molecular weight of 10-30 kD.

4. The conjugate of claim 3, wherein each of $G_1$ and $G_2$ is

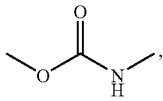

wherein O is attached to $A_1$ or $A_2$, and NH is attached to a carbon atom as shown in formula I.

5. The conjugate of claim 4, wherein P is modified interferon containing 1-4 additional amino acid residues at the N-terminus.

6. The conjugate of claim 5, wherein n is 2.

7. The conjugate of claim 6, wherein the conjugate is

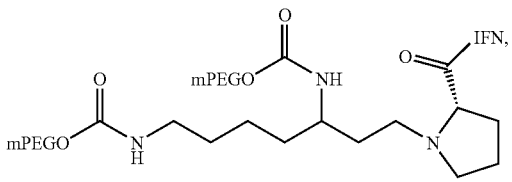

in which mPEG has a molecular weight of 20 kD and IFN is interferon-$\alpha_{2b}$.

8. A method of treating hepatitis C virus infection or hepatitis B virus infection comprising administering to a subject in need thereof an effective amount of a
protein-polymer conjugate of formula I:

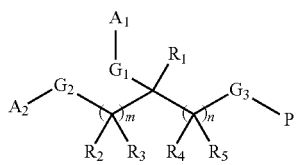

formula I wherein
each of $R_1$, $R_2$, $R_3$, $R_4$, and $R_5$ independently, is H, $C_{1-5}$ alkyl, $C_{2-5}$ alkenyl, $C_{2-5}$ alkynyl, aryl, heteroaryl, $C_{3-8}$ cycloalkyl, or $C_{3-8}$ heterocycloalkyl;
each of $A_1$ and $A_2$, independently, is a polymer;
each of $G_1$, $G_2$, and $G_3$, independently, is a bond or a linking functional group;
P is an interferon-$\alpha$;
m is 0 or an integer of 1-10; and
n is an integer of 1-10.

9. The conjugate of claim 1, wherein P is interferon-a having 1-4 additional amino acid residues at the N-terminus.

10. The conjugate of claim 1, wherein P is SEQ ID NO: 1, 2, 3, 4, or 5.

11. The conjugate of claim 1, wherein P is SEQ ID NO: 6 or 7.

12. The conjugate of claim 1, wherein P is SEQ ID NO: 8 or 9.

* * * * *